United States Patent [19]

Hatje

[11] Patent Number: 4,827,142
[45] Date of Patent: May 2, 1989

[54] METHOD AND SYSTEM FOR OPTICALLY TESTING SAWN TIMBER FOR FAULTS

[75] Inventor: Günter H. Hatje, Hamburg, Fed. Rep. of Germany

[73] Assignee: Helmut K. Pinsch GmbH & Co., Hamburg, Fed. Rep. of Germany

[21] Appl. No.: 223,690

[22] Filed: Jul. 22, 1988

Related U.S. Application Data

[63] Continuation of Ser. No. 846,591, Mar. 31, 1986, abandoned.

[30] Foreign Application Priority Data

Feb. 22, 1986 [EP] European Pat. Off. ........ 86102332.3

[51] Int. Cl.$^4$ ............................................. G01N 21/88
[52] U.S. Cl. ................................... 250/563; 356/431; 250/572
[58] Field of Search ............... 250/560, 561, 562, 563, 250/571, 572; 356/430, 431, 383; 364/475, 507

[56] References Cited

U.S. PATENT DOCUMENTS

| | | | |
|---|---|---|---|
| 3,682,554 | 8/1972 | Flaczynski | 250/560 |
| 3,840,303 | 10/1974 | Clarke | 356/431 |
| 3,920,970 | 11/1975 | Slaker | 250/563 |
| 3,976,384 | 8/1976 | Matthews et al. | 250/563 |
| 4,179,707 | 12/1979 | Sjödin | 250/560 |
| 4,188,544 | 2/1980 | Chasson | 250/560 |
| 4,260,899 | 4/1981 | Baker | 250/563 |
| 4,403,294 | 9/1983 | Hamada et al. | 250/562 |
| 4,417,149 | 11/1983 | Takeuchi et al. | 250/563 |
| 4,563,095 | 1/1986 | Puffer | 356/430 |

Primary Examiner—David C. Nelms
Assistant Examiner—William L. Oen
Attorney, Agent, or Firm—Toren, McGeady & Associates

[57] ABSTRACT

In a timber testing apparatus, use is made of an optical process, in which there is a linewise scanning of the timber surface at right angles to the longitudinal direction of the timber. If an optical detection apparatus (18) indicates a fault, the particular piece of timber is stored as being faulty at this point, so that continuous operation and detection of faults is possible in piece-related and position-related manner, so that suitable parts of the timber with a given, desired fault-free length can be rapidly determined.

11 Claims, 2 Drawing Sheets

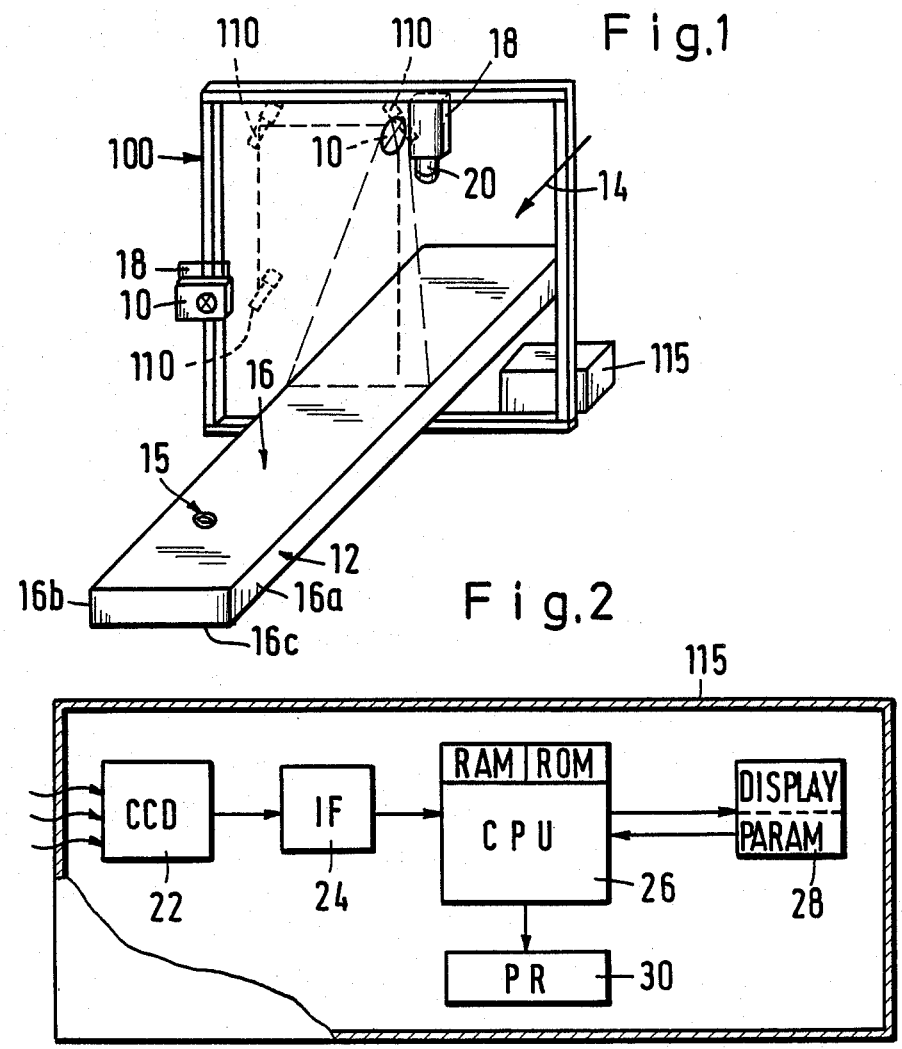
Fig. 1
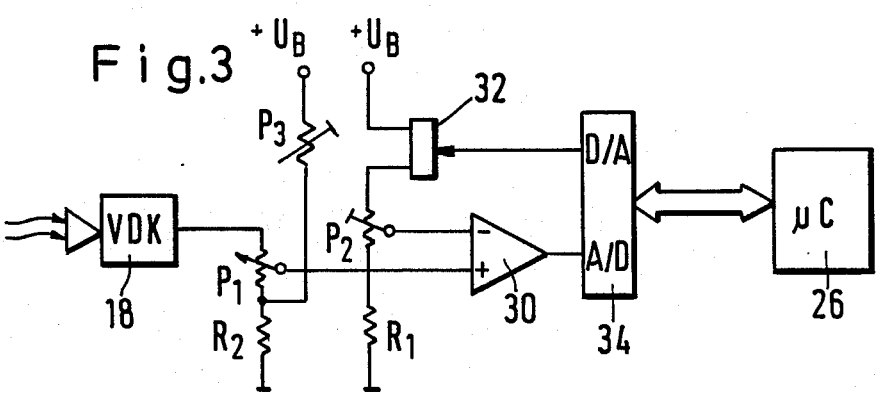
Fig. 2
Fig. 3

METHOD AND SYSTEM FOR OPTICALLY TESTING SAWN TIMBER FOR FAULTS

This is a continuation application of Ser. No. 846,591, filed Mar. 31, 1986, now abandoned.

BACKGROUND OF THE INVENTION

1. Field of the Invention

The present invention relates to a sawn timber testing apparatus system, particularly for the continuous detection of sawn timber, as well as to a process for testing such timber.

2. Description of Related Art

In known timber testing systems a mechanical momentum is given to one side of the timber plank to be tested. By means of a plurality of sensors fitted at predetermined distances from the plank, the pulse response of a shock wave produced by the same material under test is measured. The data supplied by the sensors are fed into a process computer, which determines, from the measured transit times, the modulus of elasticity of the material between the sensors. Conclusions can then be drawn regarding the existence of a fault in the wooden plank from the deviations from the standard values.

However, this process can only be used in the case of planks having the same length. If production is to be changed to different lengths for the next batch, a relatively complicated and costly adaptation is required.

In addition, this known process cannot reliably detect all the wood faults which occur in the same way. These, in fact, include color faults, which cannot be detected. Another disadvantage is that the sensors must be fitted to each plank to be measured. Thus, continuous operation is not possible with the aforementioned process.

SUMMARY OF THE INVENTION

The object of the present invention is to provide a testing system for timber, in which it is possible to reliably and rapidly detect wood surface-faults which occur, such as, for example, knots, roots, red rot, etc., which permits continuous operation and which also makes it possible to detect the faults in piece-related and position-related manner. This makes it possible to determine suitable sections with a given desired fault-free length in a rapid form, so that poorer quality timber can be used for higher quality work.

This object is achieved in a timber testing system of the aforementioned type, which, according to the invention, is constructed in such a way that at least one light source which illuminates the timber conically or with a matched geometry in a plane at right angles to its longitudinal direction and with a substantially identical intensity and in said plane is provided a line-type optical detection system which, in response to brightness and/or color changes of the illuminated timber plane during a relative high speed movement of the timber and optical detection system, supplies an information signal. It is thereby possible to carry out a point-by-point or array scanning and the light source illuminates a narrow zone extending over the width of the timber.

The optical detection system is connected to a computer having a memory where the information signals are sequentially stored, the computer determining if preset limits concerning color, size, shape, etc., are exceeded, and if so, memorizing the data.

The invention also relates to a construction in which the computer has a time or length measuring device, which measures the time or length from the detection of the leading edge of a piece of timber up to the appearance of the information signal, the time or length measuring device being linked with a memory.

The invention also provides an adapting circuit (interface), which makes it possible to adjust a detection threshold for the information signal. The matching circuit can also have control elements, for example, electronic control elements for adapting the optical detection system or light source to different background brightnesses of the timber surface or the light source using the maximum dynamics of the optical detection system. The optical detection system also has a filter for increasing the sensitivity for certain timber faults.

The optical detection system with the light source is arranged on a supporting frame, which surrounds, in annular manner, the timber to be detected. As a function of the detection surface, optical detection systems with light sources may be placed on the top and/or bottom and/or sides of the supporting frame. The possibility exists of using only a single light source and, in this case, a corresponding number of reflecting mirrors is arranged on the frame, so that only certain surfaces of the timber to be detected, or all surfaces thereof, are illuminated. This also applies to the optical detection system, which is directed via reflecting mirrors onto the surface or surfaces to be detected. Thus, apart from a number of optical detection system corresponding to the number of timber surfaces to be detected, a single optical detection system can be used and then the different light intensities of the illuminated timber surfaces can be used as a differentiating feature to show which particular surface is being detected during the detection instant so as to obtain the necessary information signal. The possibility also exists of successively detecting the different surfaces of the timber and storing the values obtained during different time intervals.

The problem is also solved by a timber testing process, which is characterized in that the timber is moved continuously in its longitudinal direction relative to a light source and an optical detection system, that the light source illuminates a narrow zone extending over the width of the timber and that the optical detection system operates in a plane at right angles to the movement direction of the timber and supplies an information signal in response to the brightness and/or color changes of the timber. The entire width of the timber can be detected in line form by the detection system. The information signal is stored in position-related manner to each tested timber portion.

Due to the fact that an optical process is used, it is additionally possible to achieve the advantage that color faults can also be recorded. Thus, it is possible to supply an information signal in response to brightness differences or color differences or a combination of brightness and color differences, which can identify the position of the particular fault. As there is no need to fit sensors to each plank, it is possible to achieve continuous operation. For example, the testing system can be constructed in fixed manner and the wood can be moved past it. Thus, it is possible to test timber at a transit speed of 3 m/s.

It is particularly advantageous that, despite continous operation, the inventive apparatus makes it possible to detect faults in piece-related or position-related manner. With respect to each piece of timber, apart from the absolute length, it is alos possible to store the faultless length, i.e. the length between any faults. If a piece of timber with a particular fault free length is required, it is possible to rapidly determine the most suitable piece of timber.

Thus, it is possible to use timber of a lower quality class in accordance with DIN 68356 for higher quality purposes.

The invention makes it unnecessary to carry out the hitherto required visual inspection of the timber, which is very tiring for the inspector's eye. It is particularly advantageous that the wood is scanned in lines or rows extending at right angles to the longitudinal direction of the timber. If a fault is detected within a line, this leads to an information signal being supplied. In addition, the position of the fault relative to the longitudinal direction of the timber is stored. It is further possible to determine the fault free length from the distance covered between two detected faults.

It is particularly advantageous if, for optical scanning purposes, use is made of a CCD measuring cell or an array or point-by-point scanning. The output signals of said cell can easily be processed and stored in a computer. It is possible to use a commercially available interface. It is also possible to carry out in a relatively simple manner, the basic brightness setting and the autofocusing. It is particularly advantageous if it is only necessary to set the fault threshold, i.e., the brightness difference from which a brightness modification is detected as a fault.

The setting of the level of brightness of the fault-free wood can take place in that, initially in a setting operating mode of the computer, a falt-free beam is passed through the testing system. The average brightness value is detected and used as a reference for further measurements. It is optionally also possible to store the position of the fault, relative to the axis of the CCD cell or the like. It is also possible to expertly inspect timber from four sides by arranging four testing systems to the left, right, above and below the timber to be tested. Due to the fact that the timber can be engaged on two or four edges, it is merely necessary to use two autofocussing means on the two other testing systems.

A further important advantage is that it is possible to test timber of a substantially random length and thickness. There are also no restrictions regarding the type of wood used, and it is also possible to store the color faults which have hitherto only been detectable by visual inspection.

It is also particularly advantageous that the measured data can be stored in an integrated system, in which, apart from the storage of the fault point, quality, dimensions and storage point of each piece of timber, it is also possible to carry out the measures necessary for commercial purposes.

BRIEF DESCRIPTION OF THE DRAWINGS

Further details, features and advantages can be gathered from the following description of embodiments relative to the drawings, wherein show:

FIG. 1 A perspective view of a first embodiment of a timber testing system.

FIG. 2 A block circuit diagram of an embodiment of a test circuit for the timber testing system.

FIG. 3 A block circuit diagram of a further embodiment of the test circuit.

DESCRIPTION OF THE PREFERRED EMBODIMENTS

Figure 4:
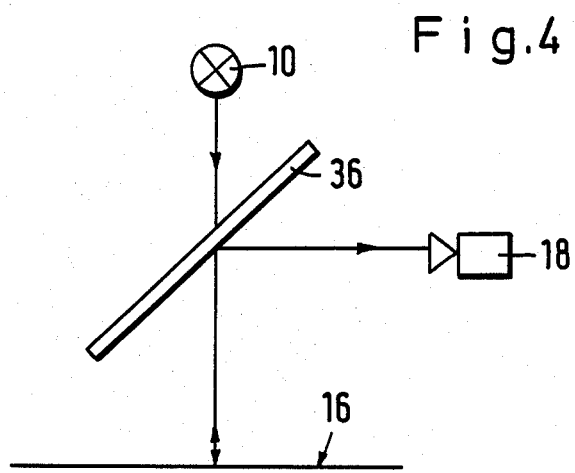
FIG. 4 A diagrammatic representation of part of the testing system.

In the embodiment of FIG. 1 a light source 1 is provided, which projects a light beam downwards onto the piece of timber 12 to be tested. The latter is movable in its longitudinal direction and is moved on guidance means (not shown), in the direction of arrow 14 at a speed of, for example, 3 m/s. The light beam from light source 10 is focused onto the surface of timber 12, the light beam extending conically, linearly or in scanned form, at right angles to the longitudinal direction of timber 12, while it is more narrowly focused in the longitudinal directionof timber 12, so that a relatively high light intensity is obtained.

Light source 10 is at such a distance from the surface 16 of timber 12 and also from fault 15 that a uniform illumination is achieved. An optical detection system 18 is positioned immediately adjacent to light source 10. The optical detection system 18 has an objective or lens 20, which is also focused onto surface 16. The arrangement of light source 10 and lens 20 with respect to one another is selected in such a way that there are no measuring errors, particularly no parallax errors. It is then possible to achieve a resolution of approximately 1 mm, even in the case of a relatively high timber conveying speed.

During the movement of the timber, surface 16 is scanned in linewise manner by the optical detection system 18, 0.3 ms being available per line of scanning. For the conversion of optical information into electrical signals, fast semiconductor line cameras can be used. In the case of reduced speed or resolution requirements, it is also possible to use less expensive, opto-electrical converters. However, it is also possible to use other scanning procedures, such as, for example, a point-by-point scan or an array scan.

It is possible to provide an optical and/or electrical filter for the optical detection system 18, which makes it possible to eliminate disturbing influences and falsifications of the test result.

As shown in FIG. 1, in the feed or advance zone of the timer 12 to be detected, a supporting frame 100 is provided which forms part of the timber testing system and receives the detection system 18 and light source 10. This supporting frame 100 can form a U-shaped profile with lateral longitudinal spars, which simultaneously form feet for the frame 100, and an upper transverse spar, which then carries the detection system 18 with the light source 10, if the surface 16 or timber 12 is to be detected. If the lateral surfaces 16a, 16b are to be detected, then detection systems and light sources must be provided on the vertical longitudinal spars of the supporting frame. If the bottom surface 16c of timber 12 is also to be detected, then use is made of an annular supporting frame 100, as shown in FIG. 1, which then also carries on its lower transverse spar a detection system and a light source.

If more than one surface of the timber 12 is to be detected, there is not need to illuminate each timber surface by means of separate light sources. One light source is then adequate and a corresponding number of reflecting mirrors 110 are provided in its optical path on frame 100 enabling one or several surfaces of the timber to be simultaneously illuminated by a single light source. In the embodiment of FIG. 1, the reflecting mirrors 110 fitted to supporting frame 100 illuminate the surface 16 of the timber. If several timber surfaces are illuminated by means of the light source 10, then separate detection systems 18 are respectively associated with each illuminated timber surface. However, it is also possible to detect several timber surfaces by means of a reflecting mirror system with only a single detection system 18. By means of different light intensities, the length of the light beam or the observation beam, it is possible to fix and individually detect the individual timber surfaces, while storing the detected values in such a way that they can subsequently be associated with the individual timber surfaces. It is also possible to detect the individual different timber surfaces in rapid time sequence and recurrent successions.

Any suitable light sources can be used as light source 10, particularly rectified light, monochromatic light, laser light, etc.

The supporting frame 100, receiving the detection system 18 and the light source 10, also receives all the further parts of the timber testing system. The test circuit is then arranged in a casing 115 connected to frame 100.

In the embodiment of a test circuit shown in FIG. 2, a CCD scanner 22 is provided as the converter. CCD scanner 22 is connected by means of a suitable interface 24 to a microcomputer 26, which has a central processing unit CPU, a random access memory RAM and a read-only memory ROM. The interface 24 serves as a matching circuit between the CCD scanner 22 and the microcomputer 26. The latter is also provided with a control unit 28, which permits the display of the measured faults and the entry of parameters for the control of fault detection. A printer 30 is also provided, which is suitable for supplying a report on the tested timbers, which can also be used when the timber has passed into stock.

Preference is given to the use of a CCD scanner 22 with 500 to 2000 pixels. Such a scanner makes it possible to scan larger wood surfaces. The actual scanning takes place in a manner known per se, so that the input signal for interface 24 is present in serial form. An A/D conversion is carried out in interface 24. The test signal associated with each scanning period is supplied in digitized form to the microcomputer 26. The microcomputer 26 checks whether, within the measured CCD cell, a measured value exceeds the fault value threshold. It is particularly advantageous if a fault value indication occurring only with an individual pixel is cancelled out, because it would most probably relate to a reflection of a wood fibre.

In addition, 8 bit resolution is adequate for the A/D converter, so that it is possible to use inexpensive technology. The microcomputer can also be constructed as a single chip component with integrated control of the peripheral equipment, which permits a further cost saving. In order to ensure troublefree operation, even under severe environmental conditions, current-saving CMOS technology can be used for the electronics.

The semiconductor memory RAM used in the microcomputer 26 can be constructed both for the intermediate storage of the detected fault points taking account of their size and position, and as a purely CPU-related main memory. The test circuit can also be used as a front-end processor in a network and, in a particularly advantageous manner, has a star structure. However, in stand-alone operation the use of an additional backing memory is also possible.

FIG. 3 provides a further embodiment of the test circuit, where the CCD scanner is replaced by a pick-up tube VDK as the optical detection system 18. The output signal of the optical detection system 18 is fed to a voltage divider $P_1$, whose output is connected to the non-inverting input of a comparator 30. The inverting input of the comparator 30 is connected to the output of a potentiometer $P_2$, which is used for the basic setting of the brightness value of the timber type tested or for adaptation to the light source being used. Potentiometer $P_2$ is also connected in series with a control member 32, which can be constructed as a field effect transistor. An automatic adaptation to the timber type to be tested is possible through control member 32. The potentiometer $P_2$ is also connected across a resistor $R_1$ to ground.

The input of control member 32 and the output of comparator 30 are connected via an integrated D/A-A/D converter 34 to microcomputer 26.

Voltage divider $P_1$ is used for setting the sensitivity of the test circuit for faults, i.e. for setting the fault threshold value. Another voltage divider is formed by a potentiometer $P_3$ and a resistor $R_2$ between the operating voltage $+U_B$ and ground. The "low" end of the voltage divider $P_1$ is connected to the center of the voltage divider formed by $P_3$ and $R_2$. Thus, the fault threshold can be fixed as a function of the setting of voltage divider $P_1$ in a relative manner, i.e. independently of the absolute value of the set brightness.

The test circuit embodiment of FIG. 3 permits the fully automatic testing of timber after initially carrying out a system-specific adjustment or alignment of trimming potentiometers $P_3$ and $P_2$. Control member 32 is set to a value corresponding to the basic brightness of the wood used. For this purpose, a fault-free or almost fault-free piece of wood of the type to be tested is initially measured in the setting operating mode of microcomputer 26. Its average brightness value is calculated by the microcomputer 26 and used for the basic setting. Switching over then takes place to the testing operating mode and a setting of the desired fault threshold is carried out using $P_1$. The fault threshold is generally dependent on the desired quality tolerance and therefore, inter alia, the type of wood to be tested. It is then possible to test the complete batch at high speed and store the fault points.

FIG. 4 shows a particularly advantageous construction of the optical detection system 18 in conjunction with light source 10. Use is made of a semireflecting mirror 36, which is arranged in the light beam so as to slope from light source 10 to surface 16. After passing through said mirror 36, the light beam from light source 10 reaches surface 16, where it is reflected. It strikes the bottom of the semireflecting mirror 36, is reflected and passed to the optical detection system 18. This construction permits a very accurate measurement of the position of the faults.

Figure 5:
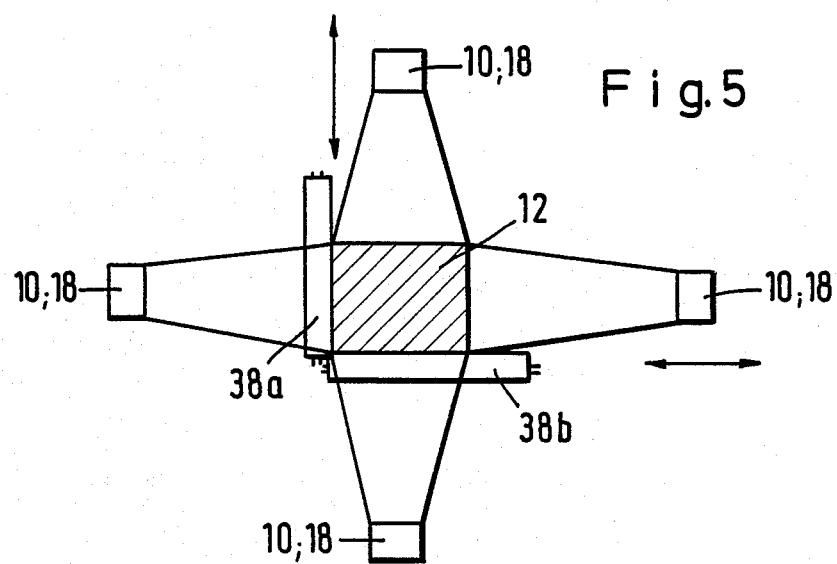
FIG. 5 A view of another embodiment of the testing system.

FIG. 5 shows another embodiment of a testing apparatus. The piece of timber 12 to be tested is a square, all of whose edges are to be investigated. For this purpose over each of the cut edges is placed one of four light sources 10 with four optical detection systems 18. Only two of the detection system 18 are provided with an autofocussing mechanism, because the distance to the wood surface with respect to the other two detection systems 18 is always the same due to the guide rollers 38a, 38b being used.

Figure 6:
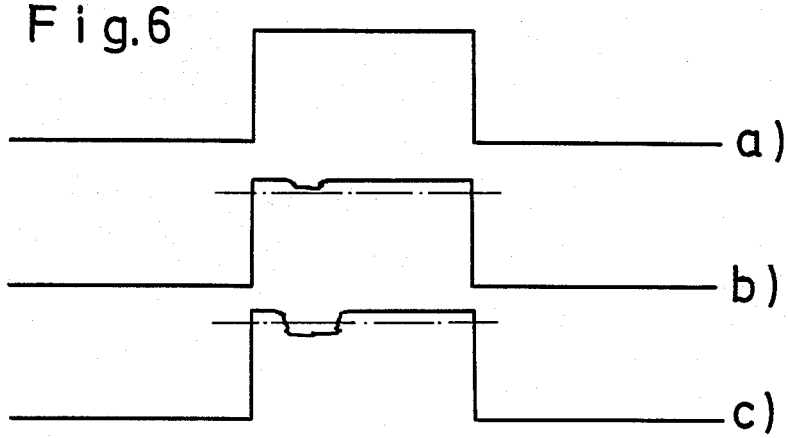
FIG. 6 Timing diagrams for representing test signals occurring in the test circuit according to FIG. 3.

FIG. 6 at (a) shows the output signal of an optical detection system in the case of a single-line scanning of a fault-free piece of wood. At (b) a fault point is reached, which can be seen through a smaller amplitude in a part of the test signal. However, the amplitude has still not dropped below the fault threshold value. (c) shows the test signal during the scanning of a test cell, which completely detects the fault. An information signal is supplied and the fault position stored. The length-related storage takes place through the microcomputer 26 measuring the time between the leading edge of the piece of timber which has just passed through and the appearance of the information signal. Due to the constant advancing speed of the piece of timber, this time is length-proportional and consequently corresponds to the length of the fault-free timber portion.

I claim:

1. A sawn timber testing system, for continuously detecting sawn timber, comprising:
    a light source for illuminating a surface of the timber in a plane at right angles to a longitudinal direction of the timber, said light source emitting a light beam which illuminates a narrow portion of said timber surface in the longitudinal direction with substantially uniform intensity, said illuminated narrow portion extending in said plane across an entire width of said surface;
    an optical detection system for detecting faults in said timber, said optical detection system being arranged in said plane and including line sensing means for detecting changes in brightness of the light beam reflected from said narrow portion simultaneously across the entire width of said surface, said optical detection system generating information signals in response to said changes;
    means for moving and guiding said said timber in said longitudinal direction; and
    computing means coupled to said optical detection system for receiving said information signal, said computing means including a memory in which said information signals are stored, said computing means determining respective positions of faults on said timber using said information signals, and storing the positions of these faults in the memory.

2. A sawn timber testing system according to claim 1, wherein said optical detection system further includes a threshold detector to which signals from said sensing means are applied, said threshold detector generating said information signals when said sensing means signals exceed a threshold level.

3. A sawn timber testing system according to claim 2, wherein said optical detection system further comprises a matching circuit for setting the threshold in said threshold detector.

4. A sawn timber testing system according to claim 3, wherein the matching circuit includes control elements for adapting the optical detection system to different basic brightnesses of the timber surface.

5. A sawn timber testing system according to claim 1, wherein the optical detection system includes a filter for increasing a sensitivity of said optical detection system for specific wood faults.

6. A sawn timber testing system according to claim 1, further comprising a plurality of said optical detection systems and light souces for simultaneously detecting faults on a plurality fo surfaces of said timber.

7. A sawn timber testing system according to claim 6, further comprising a frame surrounding said timber in said plane, said plurality of optical detection systems and said light sources being mounted on said frame opposite respective surfaces of said timber.

8. A sawn timber testing system according to claim 1, wherein said light source emits a monochromatic, rectified or laser light beam.

9. A sawn timber testing system according to claim 1, wherein said testing system further comprises a supporting frame, which carries said light source and said optical detection system, and a plurality of reflecting mirrors, arranged on said frame so that the light source illuminates the timber with substantially uniform intensity, the optical detection system detecting, via the reflecting mirrors, the illuminated surface of the timber.

10. A sawn timber testing system according to claim 9, wherein said light source emits a monochromatic, rectified or laser light beam.

11. A method for testing sawn timber, comprising the steps:
    moving said sawn timber continuously along a longitudinal direction relative to a light source and an optical detection system;
    illuminating a narrow portion of a surface of the sawn timber along a plane at right angles to said longitudinal direction extending over a width of said sawn timber with said light source;
    sensing said light beam reflected from said narrow portion simultaneously across said width of the sawn timber, detecting changes in brightness of said reflected light beam, and generating information signals in response to said changes with said optical detection system; and
    storing said information signals and determining positions on said timber of faults using said information signals.

* * * * *